(12) United States Patent
Kleinguetl et al.

(10) Patent No.: US 10,309,173 B2
(45) Date of Patent: Jun. 4, 2019

(54) IN-LINE METHODS AND APPARATUSES FOR DETERMINING THE COMPOSITION OF AN EMULSIFIED DRILLING FLUID

(71) Applicant: Halliburton Energy Services, Inc., Houston, TX (US)

(72) Inventors: Kevin Gregory Kleinguetl, Kingwood, TX (US); Dale E. Jamison, Humble, TX (US); Drew A. Fowler, Humble, TX (US); Brice Aaron Jackson, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 242 days.

(21) Appl. No.: 15/319,561

(22) PCT Filed: Feb. 2, 2016

(86) PCT No.: PCT/US2016/016158
§ 371 (c)(1),
(2) Date: Dec. 16, 2016

(87) PCT Pub. No.: WO2017/135930
PCT Pub. Date: Aug. 10, 2017

(65) Prior Publication Data
US 2018/0202246 A1 Jul. 19, 2018

(51) Int. Cl.
*G01V 1/40* (2006.01)
*E21B 21/06* (2006.01)
(Continued)

(52) U.S. Cl.
CPC .............. *E21B 21/068* (2013.01); *C09K 8/02* (2013.01); *C09K 8/36* (2013.01); *E21B 21/00* (2013.01);
(Continued)

(58) Field of Classification Search
None
See application file for complete search history.

(56) References Cited

U.S. PATENT DOCUMENTS

| | | |
|---|---|---|
| 8,058,885 B2 | 11/2011 | Caron |
| 2007/0120088 A1 | 5/2007 | Yang et al. |

(Continued)

FOREIGN PATENT DOCUMENTS

| | | |
|---|---|---|
| WO | 2012009128 A2 | 1/2012 |
| WO | 2013090875 A1 | 6/2013 |

(Continued)

OTHER PUBLICATIONS

ISR/WO for PCT/US2016/016158 dated Nov. 1, 2016.

*Primary Examiner* — Aditya S Bhat
(74) *Attorney, Agent, or Firm* — Tenley Krueger; C. Tumey Law Group PLLC

(57) ABSTRACT

Methods and apparatuses that measure thermal conductivity and electrical conductivity of a emulsified drilling fluid may be used to indirectly measure the salinity and the average specific gravity of the solids in the emulsified drilling fluid. For example, a drilling assembly may comprise a drill string extending into a wellbore penetrating a subterranean formation; a pump configured to circulate a drilling fluid through the drilling assembly; a first flow line fluidly coupling the wellbore to a retention pit; a second flow line fluidly coupling the retention pit to the pump; a third flow line fluidly coupling the pump to the drill string; and an in-line analysis system fluidly coupled to the retention pit, fluidly coupled to the second flow line, or fluidly coupled to the third flow line, the in-line analysis system comprising a thermal conductivity meter and/or an electrical conductivity meter to a sample container.

10 Claims, 3 Drawing Sheets

(51) Int. Cl.
  *C09K 8/02* (2006.01)
  *E21B 44/00* (2006.01)
  *E21B 21/00* (2006.01)
  *C09K 8/36* (2006.01)
  *E21B 47/10* (2012.01)
  *E21B 49/08* (2006.01)
  *G01F 1/712* (2006.01)
  *G01N 15/08* (2006.01)
  *G01N 29/22* (2006.01)

(52) U.S. Cl.
  CPC .......... *E21B 44/00* (2013.01); *E21B 47/1005* (2013.01); *E21B 49/082* (2013.01); *E21B 49/088* (2013.01); *G01F 1/712* (2013.01); *E21B 2049/085* (2013.01); *G01N 15/0826* (2013.01); *G01N 29/222* (2013.01)

(56) References Cited

U.S. PATENT DOCUMENTS

| | | |
|---|---|---|
| 2007/0158064 A1 | 7/2007 | Pribnow et al. |
| 2011/0303463 A1 | 12/2011 | Lessi |
| 2012/0112121 A1 | 5/2012 | Yang et al. |
| 2014/0209384 A1 | 7/2014 | Hanson |
| 2014/0333307 A1 | 11/2014 | Ahmad et al. |
| 2015/0024975 A1* | 1/2015 | Wagle .................. C09K 8/36 507/117 |
| 2015/0024976 A1 | 1/2015 | Albrighton et al. |
| 2015/0248511 A1 | 9/2015 | Suryanarayana et al. |

FOREIGN PATENT DOCUMENTS

| | | |
|---|---|---|
| WO | 2015069290 A1 | 5/2015 |
| WO | 2015105489 A1 | 7/2015 |

\* cited by examiner

IN-LINE METHODS AND APPARATUSES FOR DETERMINING THE COMPOSITION OF AN EMULSIFIED DRILLING FLUID

BACKGROUND

The present application relates to methods and apparatuses for measuring the properties of an emulsified drilling fluid.

Drilling fluids are often used to aid the drilling of wellbores into subterranean formations, for example, to remove cuttings from the borehole, control formation pressure, and cool, lubricate and support the bit and drilling assembly. Typically, the drilling fluid, which is more commonly referred to as "drilling mud" or "mud," is pumped down the borehole through the interior of the drill string, out through nozzles in the end of the bit, and then upwardly in the annulus between the drill string and the wall of the borehole. During the ascent, some of the mud congeals, forming a cake on the exposed face of the wellbore, for example, to prevent the mud from being lost to the porous drilled formation. In addition, the pressure inside the formation can be partially or fully counterbalanced by the hydrostatic weight of the mud column in the wellbore. Since the mud has a variety of vital drilling functions, it must accordingly have comparable and reliable capabilities. In the oil and gas industry, it can be important to precisely determine the characteristics and chemical compositions of drilling fluids circulating into and out of subterranean hydrocarbon-bearing formations. However, drilling fluids are often circulated through the wellbore several times where the drill cuttings, leak-off, and the like can change the composition of the drilling fluid.

Many drilling parameters, such as measured depth, string rotary speed, weight on bit, downhole torque, surface torque, flow in, surface pressure, downhole pressure, bit orientation, bit deflection, and the like, can be made available in real-time. However, the composition of the drilling fluid, which can be critical to effective hydraulic modeling and hole cleaning performance, is not readily available in real-time. Ascertaining the composition of the drilling fluid typically requires a direct measurement by a technician (or "mud engineer"). The on-site mud engineer, for example, typically has numerous other responsibilities in his/her daily routine and, therefore, cannot provide a constant stream of drilling fluid composition to a monitoring center. In addition, taking and/or generating such measurements are time consuming and inherently susceptible to human error.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present application relates to methods and apparatuses for indirectly measuring the salinity of an emulsified drilling fluid and the average specific gravity of the solids in the emulsified drilling fluid. More specifically, thermal conductivity and electrical conductivity of the emulsified drilling fluid may be measured with instrumentation in-line with the drilling system. Then, such the thermal conductivity and the electrical conductivity may be used to characterize the salinity of an emulsified drilling fluid and the average specific gravity of the solids in the emulsified drilling fluid, which may then be altered as needed to improve the performance of the emulsified drilling fluid and the efficiency of the drilling operation.

Unless otherwise specified, the term "emulsified drilling fluid" refers to drilling fluids that are (1) emulsions having a water continuous phase and an oil discontinuous phase or (2) invert emulsions having an oil continuous phase and a water discontinuous phase.

Figure 1:
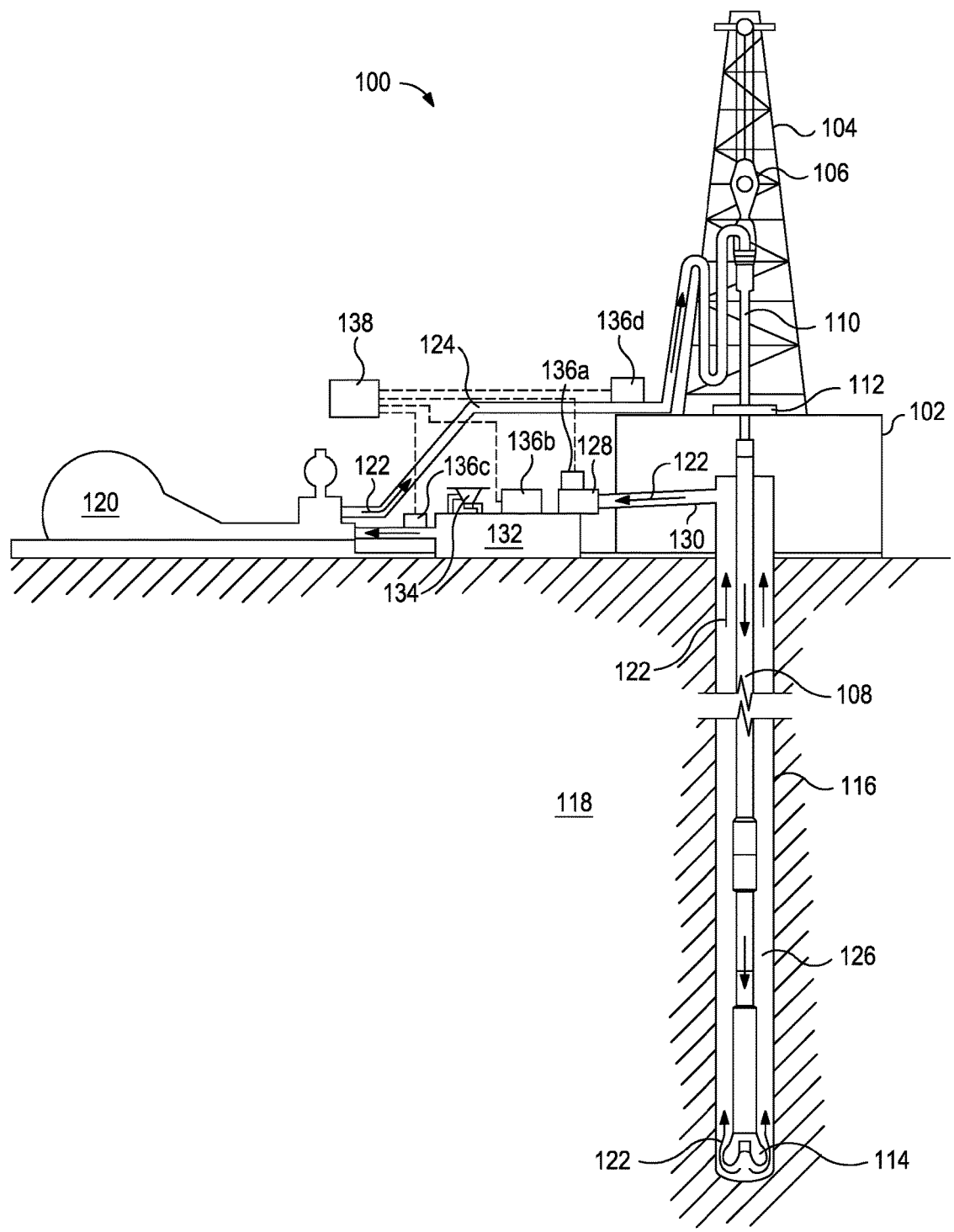
FIG. 1 illustrates a wellbore drilling system.

FIG. 1 is a wellbore drilling system 100 in accordance with at least some of the embodiments of the present disclosure. It should be noted that while FIG. 1 generally depicts a land-based drilling assembly, those skilled in the art will readily recognize that the principles described herein are equally applicable to subsea drilling operations that employ off-shore floating or sea-based platforms and rigs, without departing from the scope of the disclosure.

As illustrated, the drilling assembly 100 may include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a borehole 116 that penetrates various subterranean formations 118.

A pump 120 (e.g., a mud pump) circulates emulsified drilling fluid 122 through a feed pipe 124 and to the kelly 110, which conveys the emulsified drilling fluid 122 downhole through the interior of the drill string 108 and through one or more orifices in the drill bit 114. The emulsified drilling fluid 122 is then circulated back to the surface via an annulus 126 defined between the drill string 108 and the walls of the borehole 116. At the surface, the recirculated or spent emulsified drilling fluid 122 exits the annulus 126 and may be conveyed to various surface treatment systems (e.g., fluid processing units, retention pits, mixers, and the like). As illustrated, the spent emulsified drilling fluid 122 is conveyed to a fluid processing unit 128 via an interconnecting flow line 130. Generally, the fluid processing unit 128 cleans the emulsified drilling fluid, for example, by removing drill cuttings the emulsified drilling fluid brought to the surface. The fluid processing unit 128 may include one or more of: a shaker (e.g., shale shaker), a centrifuge, a hydrocyclone, a separator (including magnetic and electrical separators), a desilter, a desander, a separator, a filter (e.g., diatomaceous earth filters), a heat exchanger, any fluid reclamation equipment, and the like, and any combination thereof. The fluid processing unit 128 may further include one or more sensors, gauges, pumps, compressors, and the like.

After passing through the fluid processing unit 128, a "cleaned" emulsified drilling fluid 122 is deposited into a nearby retention pit 132 (i.e., a mud pit). While illustrated as being arranged at the outlet of the wellbore 116 via the annulus 126, those skilled in the art will readily appreciate that the fluid processing unit 128 and retention pit 132 may be arranged at any other location in the drilling assembly 100 to facilitate its proper function, without departing from the scope of the disclosure.

Components of the emulsified drilling fluid 122 (e.g., weighting agents and fluid loss control additives) may be added to the emulsified drilling fluid 122 via a mixing hopper 134 communicably coupled to or otherwise in fluid communication with the retention pit 132. The mixing hopper 134 may include, but is not limited to, mixers and related mixing equipment known to those skilled in the art. In other embodiments, however, the emulsified drilling fluid components may be added to the emulsified drilling fluid 122 at any other location in the drilling assembly 100. In at least one embodiment, for example, there could be more than one retention pit 132, such as multiple retention pits 132 in series. Moreover, the retention pit 132 may be representative of one or more fluid storage facilities and/or units where the emulsified drilling fluid components may be stored, reconditioned, and/or regulated until added to the emulsified drilling fluid 122.

While not illustrated, the drilling assembly 100 may further include additional downhole equipment and tools that such as, but not limited to, floats, drill collars, mud motors, downhole motors and/or pumps associated with the drill string 108, and any measurement-while-drilling or logging-while-drilling (MWD/LWD) tools and related telemetry equipment, and sensors or distributed sensors associated with the drill string 108.

The drilling assembly 100 also includes an in-line analysis system 136 (illustrated as three analysis systems 136*a-d*) communicably coupled to a control system 138 so that the control system 138 received measurements and/or data collected by the analysis system 136. The analysis system 136 and control system 138 may be co-located or physically separated in the drilling assembly 100.

The analysis system 136 may be configured to extract samples from the emulsified drilling fluid and measure the sample's thermal conductivity, electrical conductivity, or both. In some instances, the foregoing measurements may be performed at elevated temperature, elevated fluid pressure, or both. Therefore, the analysis system 136 may include a thermal conductivity meter, an electrical conductivity meter, or both equipped with or coupled to a sample container that can be heated, pressurized, or both for performing the foregoing measurements.

The illustrated drilling assembly 100 includes three analysis systems 136 with a first analysis system 136*a* fluidly coupled to the fluid processing unit 128, a second analysis system 136*b* fluidly coupled to the retention pit 132, a third analysis system 136*c* fluidly coupled to a tubular after the retention pit 132 and the mixing hopper 134, and a fourth analysis system 136*d* coupled to the feed pipe 124 before the emulsified drilling fluid 122 is introduced back into the drill string 108. The analysis systems 136 described herein may be placed at one or more of the foregoing location or at other locations along the emulsified drilling fluid flow path of the drilling assembly 100.

The placement of the first analysis system 136*a* may be useful in determining the emulsified drilling fluid salinity, the average specific gravity of the solids, or both of the emulsified drilling fluid 122 before and/or after cleaning. This may be useful in determining the amount of cleaning needed, if the cleaning was effective, or if more cleaning is needed. For example, two or more fluid analysis systems may be coupled to the fluid processing unit 128 such that measurements and analyses may be performed on fluids before and after processing by individual components of the fluid processing unit 128. By way of nonlimiting example, the fluid processing unit 128 may comprise a centrifuge and optionally a shaker upstream of the centrifuge. A fluid analysis system may be placed immediately before and another fluid analysis system may be placed immediately after the centrifuge to ascertain the performance of the centrifuge by way of the change in salinity and/or average specific gravity of the solids. It should be noted that when referring to placement being "immediately" before or after a system, tool, component, or the like, it refers to placement anywhere before or after such that the fluid being analyzed is the same compositionally as the fluid being introduced to or exiting from, respectively, the system, tool, component, or the like.

The placement of the second analysis system 136*b* may be useful in determining the emulsified drilling fluid salinity, the average specific gravity of the solids, or both of the cleaned emulsified drilling fluid 122. This may allow for determining if additional emulsified drilling fluid components (e.g., weighting agent, fluid loss control additives, or base fluid) should be added to the emulsified drilling fluid 122, for example, at the mixer 134. Additionally, placement of the first and second analysis systems 136*a,b* may be useful in controlling the solids control equipment like shakers and centrifuges based on the determination of the amount of formation solids (which lowers the average specific gravity of the solids). The first and second analysis systems 136*a,b* may be useful in determining if formation fluids are infiltrating the wellbore (e.g., a higher oil content) or if drilling fluid is leaking off into the formation. The placement of the third and fourth analysis system 136*c,d* may be useful in determining the emulsified drilling fluid salinity, the average specific gravity of the solids, or both of the emulsified drilling fluid 122 after any compositional changes. Further, this placement provides real-time measurements of the properties of the emulsified drilling fluid 122 being placed downhole, which allows for adjusting parameters of the drilling operation (e.g., weight-on-bit, emulsified drilling fluid flow rate, or drill bit rotation speed) to optimize or increase the efficiency and efficacy of the drilling operation.

In some instances, the emulsified drilling fluid salinity, the average specific gravity of the solids, or both may be measured (or otherwise derived) and compared before and after any chemical or compositional changes to the emulsified drilling fluid (e.g. at the second analysis system 136*b* and at the third and/or fourth analysis system 136*c,d*). Performing such analyses before and after chemical or compositional changes to the emulsified drilling fluid may allow for ascertaining the efficacy of the action implemented to affect the change. If the properties of the emulsified drilling fluid change more or less than expected, this may indicate an error in measurement, dosing, or inadequate mixing.

The control system 138 and corresponding computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

For example, the control system 138 described herein may be configured for receiving inputs from the analysis system 136. The processor may also be configured to perform or reference mathematical calculations, lookup tables, and offset well data comparisons that are stored on the processor to derive the water phase salinity, the average specific gravity of the solids, or both. In some instances, the processor may output a numerical value, graph, or the like indicative of the water phase salinity, the average specific gravity of the solids, or both. In some instances, the processor may change or suggest a change to the emulsified drilling fluid composition (e.g., adding additional weighting agent), the drilling operation parameters (e.g., increasing or decreasing the rate of penetration and weight on bit), or both based on the derived water phase salinity, the derived average specific gravity of the solids, or both.

In some instances, the drilling assembly 100 may further comprise other sensors that are communicably coupled to the control system 138. These sensors may provide real-time measurements of the oil-to-water ratio of the drilling fluid, the gel strength of the drilling fluid, the density of the drilling fluid, the rheology of the drilling fluid (e.g., the shear stress, the yield stress, the viscosity, the shear-thinning index, and the like), and the like, and any combination thereof. These real-time measurements may optionally be used in combination with the derived water phase salinity, the derived average specific gravity of the solids, or both when the processor makes a change or suggests a change to the emulsified drilling fluid composition (e.g., adding additional weighting agent), the drilling operation parameters (e.g., increasing or decreasing the rate of penetration and weight on bit), or both.

The foregoing drilling system 100 and those similarly designed may be used for the methods described herein. The methods may include drilling a wellbore penetrating a subterranean formation while circulating an emulsified drilling fluid through the wellbore.

The methods described herein further include measuring the thermal conductivity, the electrical conductivity, or both of the emulsified drilling fluid and calculating/deriving the water phase salinity, the average specific gravity of the solids, or both for the emulsified drilling fluid.

The thermal conductivity is a measure of the ability of the emulsified drilling fluid to conduct heat, which is dependent upon the thermal conductivity and concentration of the components of emulsified drilling fluid. The thermal conductivity of the water and oil phases of the emulsified drilling fluid are dependent on pressure and temperature. More specifically, at increased fluid pressure, the oil and water compress causing their respective thermal conductivities to change. However, the thermal conductivity of the solids (e.g., weighting agents, fluid loss control additives, and drill cuttings) in the emulsified drilling fluid are independent of pressure or are affected insignificantly compared to the fluids. Since fluids typically have a lower thermal conductivity than solids, increasing the fluid pressure compounds the foregoing effects and makes the thermal conductivity changes larger and more easily measured. Therefore, in some embodiments, the thermal conductivity of the emulsified drilling fluid may be measured at two or more fluid pressures and the difference in the thermal conductivities at the two or more fluid pressures may be calculated. Using the oil-to-water ratio, which may be known, measured, or estimated and the density of the drilling fluid, an equation similar to Maxwell's equation (Equation 1) or other methods may be used to calculate the volume of the oil phase, water phase, high gravity solids, and low gravity solids using the thermal conductivity of the drilling fluid. Then, by comparing the volume of the high gravity and low gravity solids, the average specific gravity of the solids in the emulsified drilling fluid can be calculated. If the average specific gravity of the solids is outside acceptable limits for the drilling operation, remedial actions in conditioning and cleaning the fluid to reduce the relative concentration of low gravity solids may be taken.

For example, two or more drilling fluid properties (e.g., as density, specific heat, oil-to-water ratio, percent water, pressurized thermal conductivity, various temperature thermal conductivities, and the like) may be combined with the original thermal conductivity measurement. Then, the oil phase volume, water phase volume, low gravity solids volume, and high gravity solids volume (each as absolute numbers or percentages) can be calculated using the Maxwell's equation or other methods. Then, the average specific gravity of the solids, oil-to-water ratio, density, or other numbers can be calculated, unless otherwise known.

As described above, the thermal conductivity of an emulsion or suspension depends on all components of the emulsified drilling fluid. This can be seen in Maxwell's equation (Equation 1) where $K_E$ is the effective thermal conductivity of the sample, $K_C$ is the thermal conductivity of the continuous phase, $K_D$ is the thermal conductivity of the discontinuous phase, and $\varphi_D$ is the volume fraction of the discontinuous phase.

$$K_E = K_C \left[ \frac{K_D + 2K_C - 2\varphi_D(K_C - K_D)}{K_D + 2K_C + \varphi_D(K_C - K_D)} \right]$$ Equation 1

For example, the thermal conductivity at several temperatures and/or pressures may be measured and fit to Equation 1 (or a similar equation/method) to estimate $\varphi_D$ and optionally $K_C$ and $K_D$, if not known or estimated. Then, the oil-to-water ratio and the $\varphi_D$ can be used to calculate the volume fraction of the continuous phase. Now knowing the volume fractions of the water and oil phases, the remaining volume fraction is the solids. The volume fraction of the solids and the density of the fluid may be used to determine the low gravity solids volume and high gravity solids volume. Other methods may also be used to calculate, estimate, or derive $K_C$, $K_D$, and $\varphi_D$, and ultimately the low gravity solids volume and high gravity solids volume.

Thermal conductivity may also be used to determine the salinity of the water phase of the emulsified drilling fluid because the thermal conductivity of the water phase is dependent on the salinity of the water phase. The thermal conductivity as a function of salinity for a given oil-to-water ratio at a known fluid pressure and solids content may be determined experimentally. For example, a plurality of emulsified drilling fluid samples may be prepared with different water phase salinities and their thermal conductivity measured. Then, the water phase salinities may be correlated to the thermal conductivity of the plurality of samples, thereby producing a salinity/thermal conductivity relationship. The salinity/thermal conductivity relationship may be a plot, a mathematical formula, or the like.

The thermal conductivity of the emulsified drilling fluid may be measured and correlated to the salinity based on the experimentally determined relationship for a given oil-to-water ratio at a known fluid pressure. This is possible if other properties such as the density, average specific gravity of the solids and the like are known or estimated.

Accordingly, for a more accurate salinity, the solids in the emulsified drilling fluid may be accounted for by performing the foregoing method of measuring thermal conductivity at a plurality of pressures. Once the solids content is calculated, the salinity may be calculated or otherwise estimated to account for the solids in the emulsified drilling fluid.

The electrical conductivity is a measure of the emulsified drilling fluid's ability to conduct the flow of an electrical current, which is dependent upon the electrical conductivity and concentration of the emulsified drilling fluid components. The thermal conductivity of the water and oil phases of the emulsified drilling fluid are dependent on pressure and temperature. However, for invert emulsions with an oil continuous phase, electrical conductivity is not effective to measure salinity because the water phase is discontinuous and the oil phase is not conductive. Therefore, the methods described herein use chemical avenues, physical avenues, or both for converting the invert emulsion to have a continuous water phase. For example, chemical breakers or dilution with water may be used to produce a sample with a water continuous phase. Alternatively or in combination with the foregoing, shear may be used to homogenize the sample so that the water is no longer discontinuous (i.e., to produce a broken invert emulsion drilling fluid). Then, the electrical conductivity of the sample may be measured and the salinity of the broken invert emulsion drilling fluid derived taking into account the dilution and the effect of any chemical breakers added to the sample.

In some instances, salinity may be measured as a whole for the sample. Alternatively or in addition to measuring the emulsified drilling fluid salinity, ion specific probes may be used to measure the concentration of specific salt ions. Based on the overall salinity or concentration of individual ions, remedial actions may be taken. For example, if the overall salinity is too high, which may cause the invert emulsion to break, the base invert emulsion with a water phase having a lower or no salinity may be added to the emulsified drilling fluid and homogenized. In another example, the drilling fluid may be formulated such that the water activity between the drilling fluid and the formation is managed, which may be achieved by changing or managing the water phase salinity in order to achieve wellbore stability. The driving force involved in the water transportation (for zero overbalance conditions) is the chemical potential gradient across the membrane which is generally related to the difference in solute (salt) concentration and is referred to herein as "water activity."

In some instances, the foregoing methods may be combined. For example, in some instances, the water phase salinity may be derived from the electrical conductivity methods described here, and the average specific gravity of the emulsified drilling fluid solids may be derived from the thermal conductivity methods described herein. In some instances, the water phase salinity may be derived from both electrical and thermal conductivity methods described herein, optionally in combination with deriving the average specific gravity of the emulsified drilling fluid solids with the thermal conductivity methods described herein. If the water phase salinity measurements are significantly different for the electrical and thermal conductivity methods, the user or operator may retake the measurements or do more intensive manual measurements.

Once the average specific gravity of the solids and/or the salinity of the water phase are determined by the methods described herein, a drilling parameter, the composition of the emulsified drilling fluid, a solids removal treatment, or a combination thereof may be changed based on the determined average specific gravity of the solids and/or the salinity of the water phase. Exemplary drilling parameters may include, but are not limited to, rate of penetration, string rotary speed, weight on bit, downhole torque, surface torque, flow in, surface pressure, downhole pressure, bit orientation, bit deflection, and the like, and any combination thereof. For example, if the average specific gravity of the solids is sufficiently low, the weight of the drilling fluid may be increased and unable to maintain a hydrostatic pressure for a given rate of penetration, string rotary speed, weight on bit, downhole torque, or the like. Accordingly, such drilling parameters may be changed to account for the reduced average specific gravity of the solids. Additionally or alternatively, the composition of the emulsified drilling fluid may be altered, which, for this example, may include further cleaning of the drilling fluid to reduce low gravity solids or the addition of high gravity solids.

In some instances, changing a solids removal treatment in response to the determined average specific gravity of the solids and/or the salinity of the water phase may include changing a parameter of a component in the fluid processing unit. Exemplary parameters relating to solids removal treatments that may be adjusted may include, but are not limited to, the time the emulsified drilling fluid is centrifuged, the centrifuge settings (e.g., revolutions per minute, fluid flow rate in a flow-through centrifuge, and the like) the mesh size of the shakers, the time the emulsified drilling fluid is in the retention pit, and the like, and any combination thereof.

Embodiments of the present disclosure include, but are not limited to, Embodiments A-E including combinations of Embodiments A, B, and C (e.g., A and B, B and C, A and C, or A, B, and C).

Embodiment A is a method that comprises: drilling a wellbore penetrating a subterranean formation while circulating an emulsified drilling fluid through the wellbore to surface treatment systems and back to the wellbore, the emulsified drilling fluid comprising an oil phase, a water phase, and solids; measuring a thermal conductivity of the emulsified drilling fluid in at least one location along the surface treatment systems and before circulating back into the wellbore; calculating an oil phase volume and a water phase volume for the emulsified drilling fluid based on the thermal conductivity and an oil-to-water ratio of the emulsified drilling fluid; calculating an average specific gravity of the solids based on the oil phase volume, water phase volume, and a density of the emulsified drilling fluid; and changing at least one selected from the group consisting of a drilling parameter, a composition of the emulsified drilling fluid, a solids removal treatment, and a combination thereof based on the average specific gravity of the solids.

Embodiment B is a method that comprises: drilling a wellbore penetrating a subterranean formation while circulating an emulsified drilling fluid through the wellbore to surface treatment systems and back to the wellbore, the emulsified drilling fluid comprising an oil phase, a water phase, and solids; measuring a thermal conductivity of the emulsified drilling fluid at or after the retention pit and before circulating back into the wellbore; calculating a salinity of the water phase of the emulsified drilling fluid based on the thermal conductivity of the emulsified drilling fluid and an oil-to-water ratio of the emulsified drilling fluid; and changing at least one selected from the group consisting of a drilling parameter, a composition of the emulsified drilling fluid, and a combination thereof based on the salinity of the water phase of the emulsified drilling fluid.

Embodiment C is a method that comprises: drilling a wellbore penetrating a subterranean formation while circulating an emulsified drilling fluid through the wellbore to surface treatment systems and back to the wellbore, the emulsified drilling fluid comprising an oil phase, a water phase, and solids; collecting a sample of the drilling fluid with an in-line analysis system at or after the retention pit and before circulating back into the wellbore; breaking the emulsified drilling fluid in the in-line analysis system to yield a broken emulsified drilling fluid; measuring an electrical conductivity of the broken emulsified drilling fluid; calculating a salinity of the water phase of the emulsified drilling fluid based on the electrical conductivity of the broken emulsified drilling fluid; and changing at least one selected from the group consisting of a drilling parameter, a composition of the emulsified drilling fluid, and a combination thereof based on the salinity of the water phase of the emulsified drilling fluid.

Embodiments A-C may optionally further include at least one of the following: Element 1: wherein measuring the thermal conductivity of the emulsified drilling fluid and/or the salinity of the water phase of the emulsified drilling fluid is at a plurality of fluid pressures; wherein calculating the oil phase volume and the water phase volume is based on the thermal conductivity at the plurality of fluid pressures and an oil-to-water ratio of the emulsified drilling fluid; Element 2: wherein the emulsified drilling fluid is at an elevated temperature relative to ambient temperature when measuring the thermal conductivity and/or electrical conductivity of the emulsified drilling fluid; Element 3: wherein the emulsified drilling fluid is at a reduced temperature relative to ambient temperature when measuring the thermal conductivity and/or electrical conductivity of the emulsified drilling fluid; Element 4: wherein the surface treatment systems include a fluid processing unit upstream of a retention pit, and wherein measuring the thermal conductivity and/or electrical conductivity is at the fluid processing unit; Element 5: Element 4 and wherein the fluid processing unit comprises a centrifuge, wherein the thermal conductivity and/or electrical conductivity is a first thermal conductivity and/or electrical conductivity and the average specific gravity of the solids and/or salinity of the water phase of the emulsified drilling fluid is the first average specific gravity of the solids and/or salinity of the water phase of the emulsified drilling fluid, and wherein measuring the first thermal conductivity and/or electrical conductivity immediately before the centrifuge and the method further includes measuring a second thermal conductivity and/or electrical conductivity immediately after the centrifuge, and calculating a second average specific gravity of the solids and/or salinity of the water phase of the emulsified drilling fluid based on the second thermal conductivity and/or electrical conductivity; Element 6: wherein the surface treatment systems include a fluid processing unit upstream of a retention pit, and wherein measuring the thermal conductivity and/or electrical conductivity is at the retention pit; and Element 7: wherein the surface treatment systems include a retention pit upstream of a mixer, and wherein measuring the thermal conductivity and/or electrical conductivity is downstream of the mixer. Exemplary combinations may include, but are not limited to, Element 1 in combination with Element 2 or Element 3; Element 4 in combination with Element 2 or Element 3; Element 1 and Element 4 in combination and optionally in further combination with Element 5 and/or one of Element 2 or Element 3; Element 1 and Element 4 in combination and optionally in further combination with Element 5 and/or Element 6; Element 1 and Element 4 in combination and optionally in further combination with Element 5 and/or Element 7; Element 1 or Element 4 in combination with Element 6 or Element 7, and the like.

Embodiment B may optionally further comprise: preparing a plurality of samples of the emulsified drilling fluid with different water phase salinities; measuring a thermal conductivity of the plurality of samples; correlating the water phase salinities to the thermal conductivity of the plurality of samples, thereby producing a salinity/thermal conductivity relationship; wherein calculating the salinity of the water phase of the emulsified drilling fluid is further based on the salinity/thermal conductivity relationship and optionally measuring the thermal conductivity of the emulsified drilling fluid at or after the retention pit and before circulating back into the wellbore; calculating an oil phase volume and a water phase volume for the emulsified drilling fluid based on the thermal conductivity and the oil-to-water ratio of the emulsified drilling fluid; calculating an average specific gravity of the solids based on the oil phase volume, water phase volume, and a density of the emulsified drilling fluid; and changing at least one selected from the group consisting of a drilling parameter, a composition of the emulsified drilling fluid, and a combination thereof based on the salinity of the water phase of the emulsified drilling fluid and the average specific gravity of the solids.

Embodiment C may optionally further comprise: wherein breaking the emulsified drilling fluid involves diluting the emulsified drilling fluid with known quantities of water and homogenizing the emulsified drilling fluid.

Embodiment D is a drilling assembly that comprises: a drill string extending into a wellbore penetrating a subterranean formation; a pump configured to circulate a drilling fluid through the drilling assembly; a first flow line fluidly coupling the wellbore to a retention pit; a second flow line fluidly coupling the retention pit to the pump; a third flow line fluidly coupling the pump to the drill string; and an in-line analysis system fluidly coupled to the retention pit, fluidly coupled to the second flow line, or fluidly coupled to the third flow line, the in-line analysis system comprising a thermal conductivity meter, an electrical conductivity meter, or both coupled to a sample container.

Embodiment E is an in-line analysis system comprising: an analysis unit selected from the group consisting of a thermal conductivity meter, an electrical conductivity meter, and any combination thereof; and a processor communicably coupled to the analysis unit and including a non-transitory, tangible, computer-readable storage medium containing a program of instructions that cause a computer system running the program of instructions to: receive one selected from the group consisting of a thermal conductivity of an emulsified drilling fluid from the thermal conductivity meter, an electrical conductivity of the emulsified drilling fluid from the electrical conductivity meter, an electrical conductivity of a broken emulsified drilling fluid from the electrical conductivity meter, and any combination thereof; perform at least one selected from the group consisting of: (A) calculate an oil phase volume and a water phase volume for the emulsified drilling fluid based on the thermal conductivity and an oil-to-water ratio of the emulsified drilling fluid; calculate an average specific gravity of the solids based on the oil phase volume, water phase volume, and a density of the emulsified drilling fluid; (B) calculate a salinity of the water phase of the emulsified drilling fluid based on the thermal conductivity of the emulsified drilling fluid and an oil-to-water ratio of the emulsified drilling fluid; and (C) calculating a salinity of the water phase of the emulsified drilling fluid based on the electrical conductivity of the broken emulsified drilling fluid; change at least one selected from the group consisting of a drilling parameter, a composition of the emulsified drilling fluid, a solids removal treatment, and any combination thereof based on one selected from the group consisting of the average specific gravity of the solids, the salinity of the water phase of the emulsified drilling fluid, and any combination thereof.

In some instances, the drilling assembly of Embodiment D and the in-line analysis system of Embodiment E may optionally be altered for performing one or more of Embodiments A-C including any additional, optional elements. For example, the drilling assembly of Embodiment D and the in-line analysis system of Embodiment E may optionally be configured for diluting the emulsified drilling fluid to form the broken emulsified drilling fluid. For example, the program of instructions of Embodiment E may also include instructions to add water to a sample of the drilling fluid before measuring the electrical conductivity of the broken emulsified drilling fluid.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Example 1

Multiple invert emulsion drilling fluids were prepared in the laboratory with varying oil-to-water ratios, average specific gravity of the solids, water phase salinities, and densities. The thermal conductivity of each sample was measured. Using the thermal conductivity, the oil-to-water ratio (known), and the density of each sample (known), the average specific gravity of the solids was calculated using a modified version of Maxwell's equation. Other methods could have been used to predict the average specific gravity of the solids such as look up tables, neural networks, and the like. Table 1 provides the known values of oil-to-water ratio, density, and water phase salinity; measured thermal conductivity (TC); and actual and predicted average specific gravity (ASG) of the solids with percent error.

TABLE 1

| Density (ppg) | Oil-to-Water Ratio | Salinity (k ppm) | Measured TC (W/mK) | Actual ASG | Pred. ASG | % Error |
|---|---|---|---|---|---|---|
| 10 | 75:25 | 250 | 0.243 | 3.59 | 3.63 | 0.93 |
| 10 | 85:15 | 250 | 0.219 | 3.64 | 3.51 | 3.76 |
| 13 | 75:25 | 150 | 0.298 | 3.91 | 4.02 | 3.06 |
| 13 | 85:15 | 200 | 0.273 | 3.91 | 3.90 | 0.15 |
| 13 | 85:15 | 250 | 0.273 | 3.90 | 3.88 | 0.52 |
| 13 | 95:5 | 150 | 0.25 | 3.92 | 3.80 | 3.18 |
| 13 | 95:5 | 250 | 0.252 | 3.92 | 3.76 | 4.07 |
| 16 | 75:25 | 200 | 0.36 | 4.00 | 4.16 | 3.93 |
| 16 | 85:15 | 150 | 0.333 | 4.01 | 4.12 | 2.80 |
| 16 | 95:5 | 250 | 0.316 | 4.01 | 3.99 | 0.44 |
| 16 | 85:15 | 250 | 0.359 | 3.86 | 3.87 | 0.16 |
| 16 | 85:15 | 250 | 0.364 | 3.74 | 3.82 | 2.30 |
| 16 | 85:15 | 250 | 0.341 | 4.00 | 4.02 | 0.55 |

This example illustrates that using thermal conductivity measurements, the average specific gravity of the solids in an emulsified drilling fluid can be predicted with reasonable accuracy (4% or less error). The thermal conductivity method is faster and less labor intensive than measuring the actual average specific gravity of the solids in the field, which may involve time consuming testing. Therefore, the thermal conductivity method described herein may be advantageously implemented in the field for real-time or near-real-time measurements/estimates of the average specific gravity of the solids in a drilling fluid.

Example 2

Figure 2:
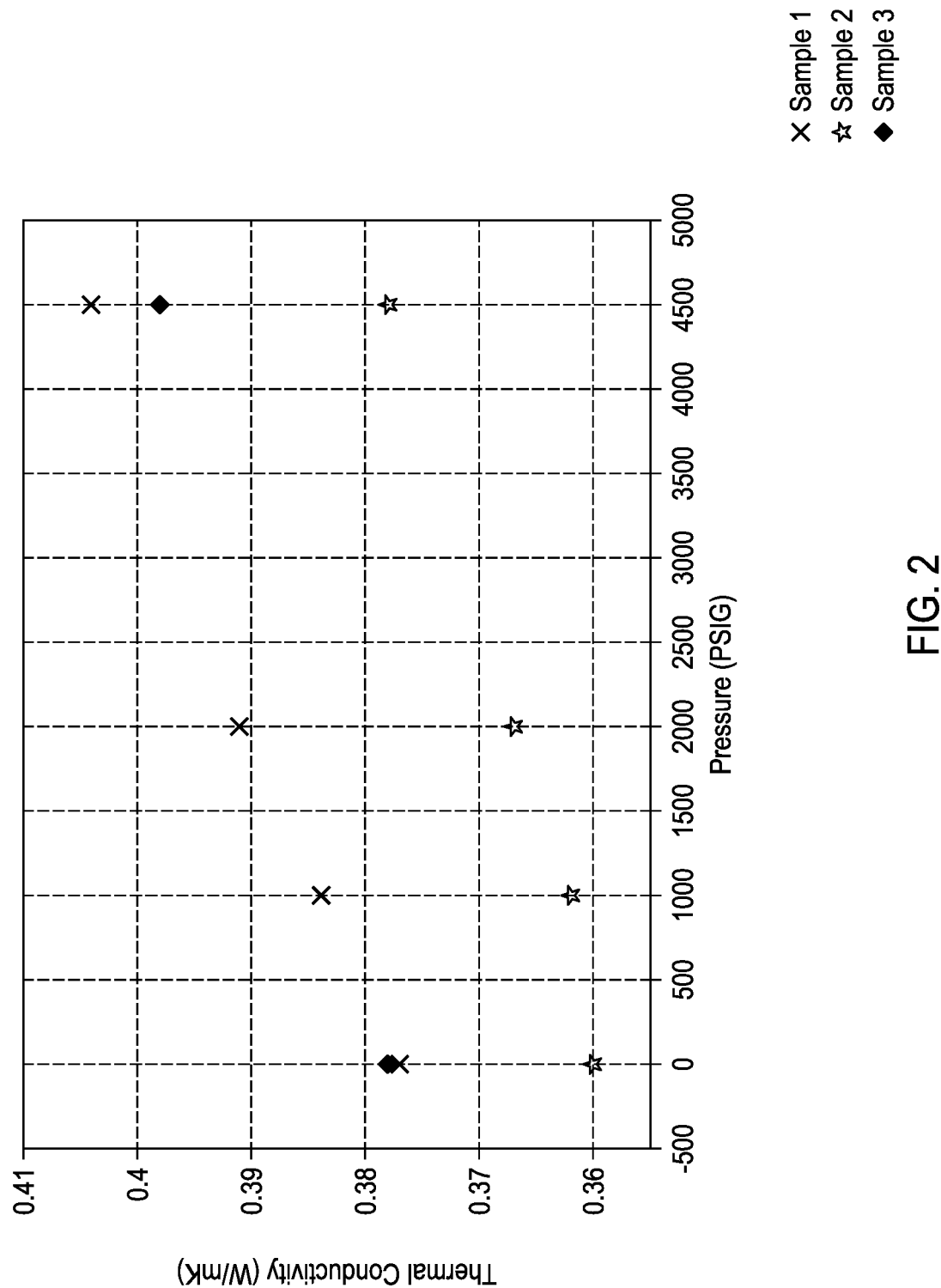
FIG. 2 provides a graph of the thermal conductivity of several emulsified drilling fluid samples as a function of fluid pressure.

Three invert emulsion drilling fluid samples were obtained from the field. Sample 1—16 ppg (pounds per gallon) drilling fluid with a 77:23 oil-to-water ratio with an average specific gravity of the solids of 3.87, Sample 2—13.75 ppg drilling fluid with a 71:29 oil-to-water ratio using solids having an average specific gravity of 3.29, and Sample 3—12.8 ppg drilling fluid with a 50.1:49.9 oil-to-water ratio using solids having an average specific gravity of 2.86. The thermal conductivity of each sample was measured at two or more fluid pressures. FIG. 2 provides a graph of the measured thermal conductivities as a function of fluid pressure. For each sample, the thermal conductivity increases with increasing fluid pressure. It is important to note that each sample has a different initial thermal conductivity as well as a different change in thermal conductivity reflecting their different oil-to-water ratios and average specific gravities of solids. Looking at changes in thermal conductivity as well as absolute thermal conductivities, it is possible to reduce the required inputs (i.e., estimating or measuring the oil-to-water ratio) using the changes in the thermal conductivity due to changes in pressure for each sample, or the slope of the thermal conductivity as a function of applied fluid pressure plot. The average specific gravity for each sample can be calculated using Maxwell's equation or other methods to yield: Sample 1—3.80 average specific gravity, Sample 2—3.41 average specific gravity, and Sample 2—2.95 average specific gravity. The average specific gravity for the solids in each sample as derived from the thermal conductivity is less than 5% from the actual average specific gravity. Further, for an in-line analysis system, these measurements could be taken in typically less than 5 minutes for each sample. This example demonstrates that thermal conductivity may be used to derive the average specific gravity of the solids in an emulsified drilling fluid and may be implemented in a drilling system for real-time measurements and analyses.

Example 3

Figure 3:
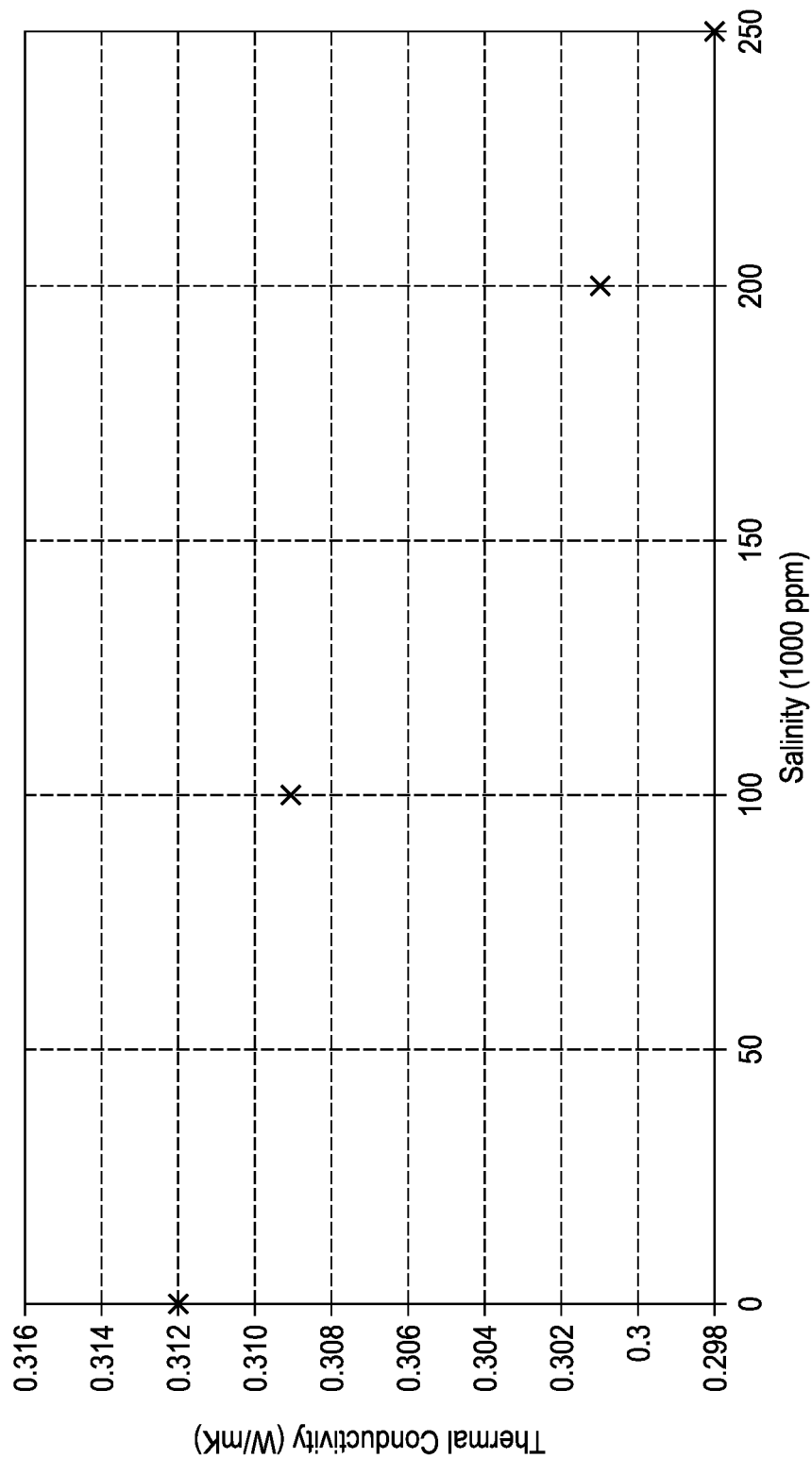
FIG. 3 is a plot of thermal conductivity as a function of salinity of the water phase for invert emulsion drilling fluids.

Several invert emulsion drilling fluid samples were prepared to be identical except for the salinity of the water phase. The thermal conductivity of each was measured for each sample at atmospheric pressure. FIG. 3 is a plot of thermal conductivity as a function of salinity of the water phase of an invert emulsion. The thermal conductivity of the invert emulsion drilling fluid decreases with increasing salinity. Further, for an in-line analysis system, a thermal conductivity measurement could be taken in less than a minute. This example demonstrates that thermal conductivity may be used to derive the salinity of an emulsified drilling fluid and may be implemented in a drilling system for real-time measurements and analyses.

Example 4

Four invert emulsion drilling fluid samples were prepared using oil as the continuous phase, different salinity brines for the discontinuous phase, barite as the weighting agent, and some additional additives to emulsify the samples. The salinity of the samples were measured by (1) the standard laboratory titration method, which can take over 30 minutes per sample, and (2) electrical conductivity after dilution with 5 mL of deionized water per 1 mL of sample and high shear mixing. Table 2 provides the water phase salinity (WPS) measured by each method and the actual water phase salinity.

TABLE 2

| Sample | Actual WPS | WPS Measured via Dilution Method | WPS Measured via Titration Method |
|---|---|---|---|
| 1 | 257.7k ppm | 252.3k ppm | 261k ppm |
| 2 | 200k ppm | 193.9k ppm | 195k ppm |
| 3 | 100k ppm | 107.9k ppm | 73.3k ppm |
| 4 | 0k ppm | 6.85k ppm | 20k ppm |

For an in-line analysis system, a dilution and electrical conductivity measurement could be taken in less than a few minutes. This example demonstrates that electrical conductivity may be used to derive the salinity of an emulsified drilling fluid and may be implemented in a drilling system for real-time measurements and analyses.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:
1. A method comprising:
   drilling a wellbore penetrating a subterranean formation while circulating an emulsified drilling fluid through the wellbore to surface treatment systems and back to the wellbore, the emulsified drilling fluid comprising an oil phase, a water phase, and solids;

measuring a thermal conductivity of the emulsified drilling fluid in at least one location along the surface treatment systems and before circulating back into the wellbore;

calculating an oil phase volume and a water phase volume for the emulsified drilling fluid based on the thermal conductivity and an oil-to-water ratio of the emulsified drilling fluid;

calculating an average specific gravity of the solids based on the oil phase volume, water phase volume, and a density of the emulsified drilling fluid; and changing at least one selected from the group consisting of a drilling parameter, a composition of the emulsified drilling fluid, a solids removal treatment, and a combination thereof based on the average specific gravity of the solids.

2. The method of claim 1, wherein measuring the thermal conductivity of the emulsified drilling fluid is at a plurality of fluid pressures; wherein calculating the oil phase volume and the water phase volume is based on the thermal conductivity at the plurality of fluid pressures and an oil-to-water ratio of the emulsified drilling fluid.

3. The method of claim 1, wherein the emulsified drilling fluid is at an elevated temperature relative to ambient temperature when measuring the thermal conductivity of the emulsified drilling fluid.

4. The method of claim 1, wherein the emulsified drilling fluid is at a reduced temperature relative to ambient temperature when measuring the thermal conductivity of the emulsified drilling fluid.

5. The method of claim 1, wherein the surface treatment systems include a fluid processing unit upstream of a retention pit, and wherein measuring the thermal conductivity is at the fluid processing unit.

6. The method of claim 5, wherein the fluid processing unit comprises a centrifuge, wherein the thermal conductivity is a first thermal conductivity and the average specific gravity of the solids is the first average specific gravity of the solids, and wherein measuring the first thermal conductivity immediately before the centrifuge and the method further includes measuring a second thermal conductivity immediately after the centrifuge, and calculating a second average specific gravity of the solids based on the second thermal conductivity.

7. The method of claim 1, wherein the surface treatment systems include a fluid processing unit upstream of a retention pit, and wherein measuring the thermal conductivity is at the retention pit.

8. The method of claim 1, wherein the surface treatment systems include a retention pit upstream of a mixer, and wherein measuring the thermal conductivity is downstream of the mixer.

9. An in-line analysis system comprising:
an analysis unit selected from the group consisting of a thermal conductivity meter, an electrical conductivity meter, and any combination thereof; and
a processor communicably coupled to the analysis unit and including a non-transitory, tangible, computer-readable storage medium containing a program of instructions that cause a computer system running the program of instructions to:
receive one selected from the group consisting of a thermal conductivity of an emulsified drilling fluid from the thermal conductivity meter, an electrical conductivity of the emulsified drilling fluid from the electrical conductivity meter, an electrical conductivity of a broken emulsified drilling fluid from the electrical conductivity meter, and any combination thereof;
perform at least one selected from the group consisting of:
(A) calculate an oil phase volume and a water phase volume for the emulsified drilling fluid based on the thermal conductivity and an oil-to-water ratio of the emulsified drilling fluid; calculate an average specific gravity of the solids based on the oil phase volume, water phase volume, and a density of the emulsified drilling fluid;
(B) calculate a salinity of the water phase of the emulsified drilling fluid based on the thermal conductivity of the emulsified drilling fluid and an oil-to-water ratio of the emulsified drilling fluid; and
(C) calculating a salinity of the water phase of the emulsified drilling fluid based on the electrical conductivity of the broken emulsified drilling fluid;
change at least one selected from the group consisting of a drilling parameter, a composition of the emulsified drilling fluid, a solids removal treatment, and any combination thereof based on one selected from the group consisting of the average specific gravity of the solids, the salinity of the water phase of the emulsified drilling fluid, and any combination thereof.

10. A drilling assembly comprising:
a drill string extending into a wellbore penetrating a subterranean formation;
a pump configured to circulate a drilling fluid through the drilling assembly;
a first flow line fluidly coupling the wellbore to a retention pit;
a second flow line fluidly coupling the retention pit to the pump;
a third flow line fluidly coupling the pump to the drill string; and
an in-line analysis system of claim 9 fluidly coupled to the retention pit, fluidly coupled to the second flow line, or fluidly coupled to the third flow line, the in-line analysis system comprising a thermal conductivity meter, an electrical conductivity meter, or both coupled to a sample container.

* * * * *